United States Patent [19]
Malis et al.

[11] Patent Number: 5,733,283
[45] Date of Patent: Mar. 31, 1998

[54] FLAT LOOP BIPOLAR ELECTRODE TIPS FOR ELECTROSURGICAL INSTRUMENT

[76] Inventors: Jerry L. Malis, 300 Valley Forge Cir., Penthouse 43, King of Prussia, Pa. 19406; Martin T. Mortimer, 41 Indian Valley La., Telford, Pa. 18969; Leonard Malis, 219-44 Peck Ave., Queens, N.Y. 11427

[21] Appl. No.: 658,429

[22] Filed: Jun. 5, 1996

[51] Int. Cl.⁶ ..................................................... A61B 17/39
[52] U.S. Cl. ............................................. 606/48; 606/50
[58] Field of Search .................................. 606/41, 45, 46, 606/48–50, 29, 30; 219/233, 236–239

[56] References Cited

U.S. PATENT DOCUMENTS

| | | |
|---|---|---|
| 2,377,540 | 6/1945 | Costa ............................. 606/45 |
| 3,234,356 | 2/1966 | Babb ............................. 219/233 |
| 3,526,750 | 9/1970 | Siegel ............................ 219/233 |
| 3,647,584 | 3/1972 | Duffy . |
| 3,679,500 | 7/1972 | Kubo et al. . |
| 3,708,295 | 1/1973 | Schumacher . |
| 3,738,879 | 6/1973 | Siemens . |
| 3,813,310 | 5/1974 | Droege et al. . |
| 3,839,108 | 10/1974 | Leinkram . |
| 3,901,242 | 8/1975 | Storz . |
| 3,959,527 | 5/1976 | Droege . |
| 3,970,088 | 7/1976 | Morrison . |
| 3,987,795 | 10/1976 | Morrison . |
| 4,043,342 | 8/1977 | Morrison, Jr. . |
| 4,051,855 | 10/1977 | Schneiderman . |
| 4,060,087 | 11/1977 | Hiltebrandt et al. . |
| 4,074,718 | 2/1978 | Morrison, Jr. . |
| 4,116,198 | 9/1978 | Roos . |
| 4,161,950 | 7/1979 | Doss et al. . |
| 4,202,337 | 5/1980 | Hren et al. . |
| 4,228,800 | 10/1980 | Degler, Jr. et al. . |
| 4,232,676 | 11/1980 | Herczog . |
| 4,248,231 | 2/1981 | Herczog et al. . |
| 4,269,174 | 5/1981 | Adair . |
| 4,301,802 | 11/1981 | Poler . |
| 4,380,876 | 4/1983 | Strassburg . |
| 4,482,426 | 11/1984 | Maynard et al. . |
| 4,532,924 | 8/1985 | Auth et al. . |
| 4,548,207 | 10/1985 | Reimels . |
| 4,578,318 | 3/1986 | Schoch et al. . |
| 4,637,390 | 1/1987 | Sorochenko . |
| 4,637,392 | 1/1987 | Sorochenko . |
| 4,651,734 | 3/1987 | Doss et al. . |
| 4,674,498 | 6/1987 | Stasz . |
| 4,674,499 | 6/1987 | Pao . |
| 4,684,438 | 8/1987 | Lazzari . |
| 4,686,980 | 8/1987 | Williams et al. . |
| 4,706,667 | 11/1987 | Roos . |
| 4,711,239 | 12/1987 | Sorochenko et al. . |
| 4,711,800 | 12/1987 | DiVincenzo . |
| 4,765,331 | 8/1988 | Petruzzi . |
| 4,802,476 | 2/1989 | Noerenberg et al. . |
| 4,805,616 | 2/1989 | Pao . |
| 4,818,962 | 4/1989 | Molaine et al. . |
| 4,823,791 | 4/1989 | D'Amelio et al. . |
| 4,860,745 | 8/1989 | Farin et al. . |
| 4,862,890 | 9/1989 | Stasz et al. . |
| 4,876,110 | 10/1989 | Blanch . |
| 4,905,691 | 3/1990 | Rydell . |
| 4,922,903 | 5/1990 | Welch et al. . |
| 4,936,281 | 6/1990 | Stasz . |
| 4,936,842 | 6/1990 | D'Amelio et al. . |
| 5,009,656 | 4/1991 | Reimels . |
| 5,013,312 | 5/1991 | Parins et al. . |

(List continued on next page.)

*Primary Examiner*—Lee S. Cohen
*Attorney, Agent, or Firm*—Panitch Schwarze Jacobs & Nadel, P.C.

[57] ABSTRACT

An electrode tip is provided for use in a bi polar electrosurgical instrument. The electrode tip has a generally loop shaped working portion, including a first and second electrode. The first electrode is generally loop shaped. The second electrode generally surrounds the first electrode and is generally spaced from and coplanar with the first electrode. The electrodes have sharp edges in cross-section which emit concentrated energy in the radial direction.

44 Claims, 6 Drawing Sheets

U.S. PATENT DOCUMENTS

| | | |
|---|---|---|
| 5,071,419 | 12/1991 | Rydell et al. . |
| 5,073,233 | 12/1991 | Banks et al. . |
| 5,084,045 | 1/1992 | Helenowski . |
| 5,089,002 | 2/1992 | Kirwan, Jr. . |
| 5,120,396 | 6/1992 | Chen . |
| 5,125,927 | 6/1992 | Belanger . |
| 5,171,311 | 12/1992 | Rydell et al. . |
| 5,192,280 | 3/1993 | Parins . |
| 5,197,964 | 3/1993 | Parins . |
| 5,269,782 | 12/1993 | Sutter . |
| 5,282,799 | 2/1994 | Rydell . |
| 5,290,285 | 3/1994 | Kirwan, Jr. . |
| 5,290,286 | 3/1994 | Parins . |
| 5,302,234 | 4/1994 | Grace et al. . |
| 5,317,938 | 6/1994 | de Juan, Jr. et al. . |
| 5,318,563 | 6/1994 | Malis et al. . |
| 5,318,564 | 6/1994 | Eggers . |
| 5,354,422 | 10/1994 | Kato et al. . |
| 5,437,665 | 8/1995 | Munro ........................ 606/45 |
| 5,451,224 | 9/1995 | Goble et al. ................. 606/48 |
| 5,569,244 | 10/1996 | Hahnen ....................... 606/46 |
| 5,593,406 | 1/1997 | Eggers et al. ................ 606/29 |

FOREIGN PATENT DOCUMENTS

| | | |
|---|---|---|
| 0 280 972 A1 | 2/1988 | European Pat. Off. . |
| 0 294 063 A2 | 5/1988 | European Pat. Off. . |
| 252 284 A3 | 3/1984 | German Dem. Rep. . |
| 257 348 A3 | 3/1984 | German Dem. Rep. . |
| 2525982 | 12/1976 | Germany ..................... 606/46 |
| WO93/13719 | 7/1993 | WIPO . |

OTHER PUBLICATIONS

Brochure entitled "Photo Chemical Machining", Buckbee–Mears, St. Paul, A Unit of BMC Industries, Inc., St. Paul, MN, 1995, 2 pages.

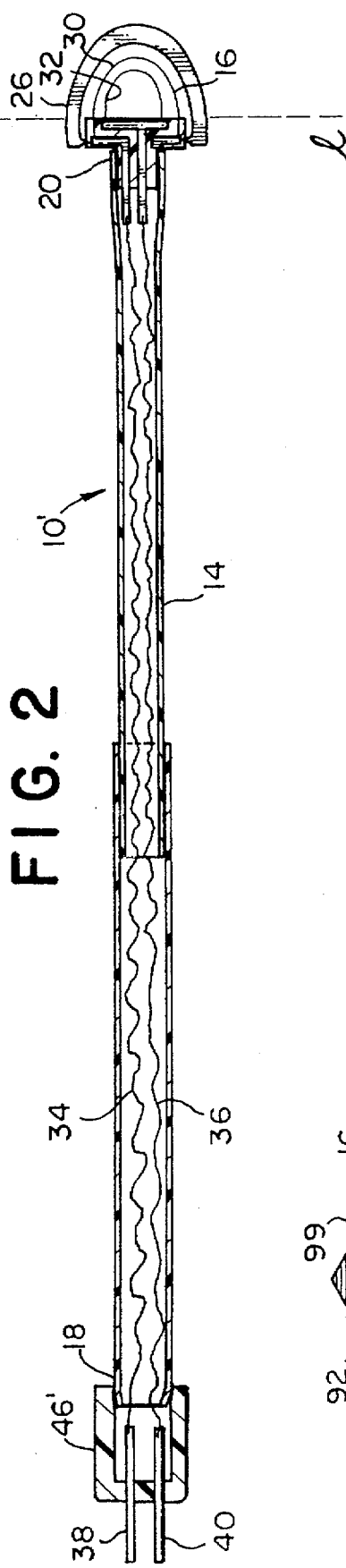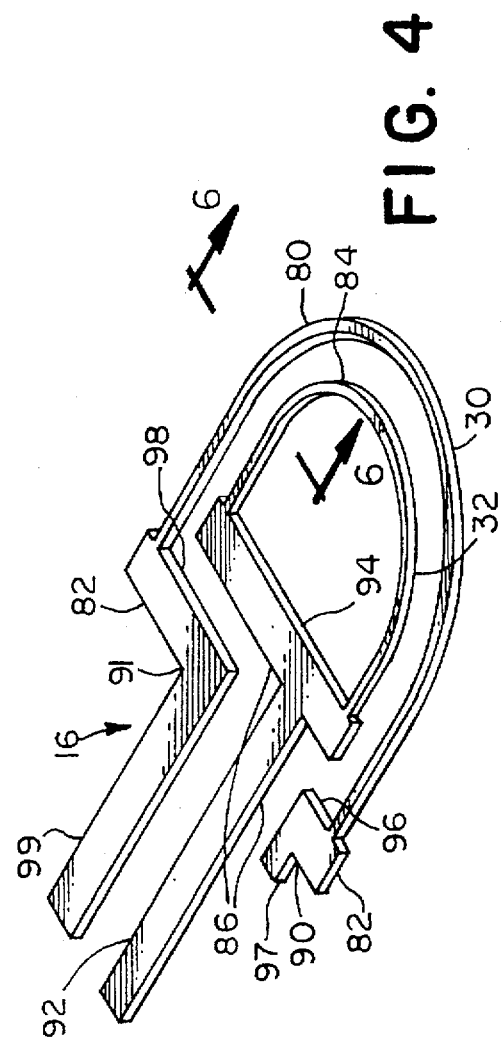

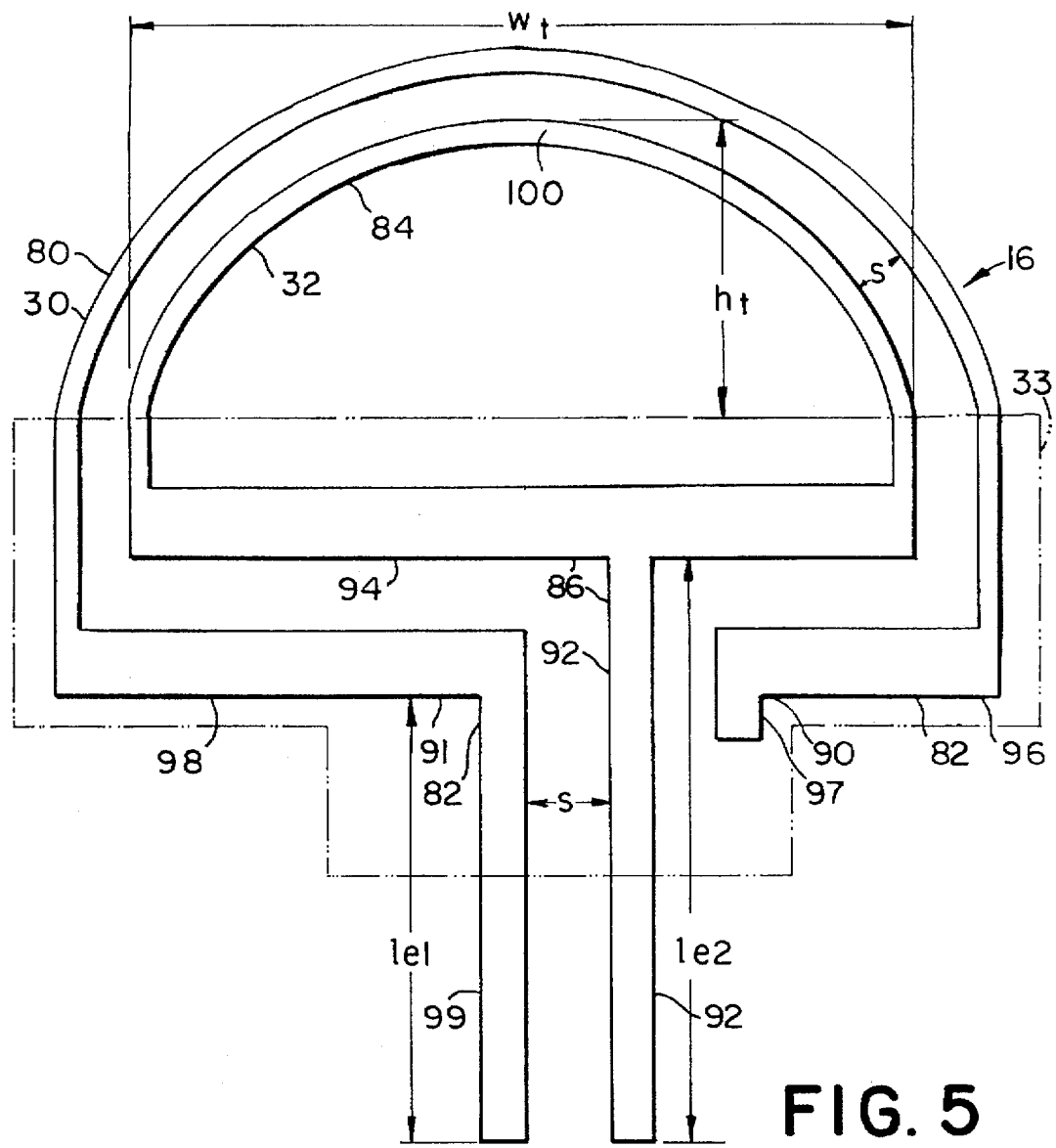
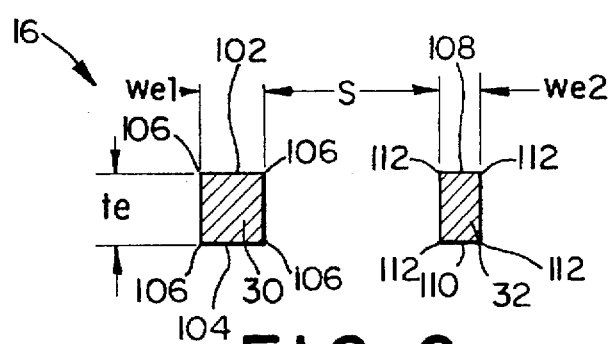
FIG. 5
FIG. 6

FLAT LOOP BIPOLAR ELECTRODE TIPS FOR ELECTROSURGICAL INSTRUMENT

FIELD OF THE INVENTION

The present invention relates generally to electrosurgical instruments, and, in particular to an electrode tip for a bipolar electrosurgical cutting/coagulating instrument particularly adaptable for use in constricted areas and a method of making an electrode tip by a photo chemical machining process.

BACKGROUND OF THE INVENTION

Electrosurgery is one form of a surgical cutting and coagulating procedure. Electrosurgery has two primary modes—monopolar and bipolar. Monopolar surgery uses an instrument, with a single electrode such as a single loop instrument, and a grounding pad as the means to administer the output of a surgical generator to the patient. In contrast, bipolar instruments include two electrodes in close proximity to each other. Typically, one electrode is a supply electrode and the other electrode is a return electrode. Bipolar instruments operate at much lower power levels than monopolar instruments and thus do not disturb nearby tissue. Examples of bipolar instruments are shown in U.S. Pat. Nos. 5,290,286 (Parins); 5,192,280 (Parins); 5,013,312 (Parins et al.); 5,282,799 (Rydell); 5,071,419 (Rydell) and WO 93/13719 (Fleenor et al.).

Wire electrodes, which are used in some such instruments, are generally rounded in cross-section and thus do not concentrate energy in any particular radial direction. Rounded electrodes also present a relatively large contact area to the surgical site. This may be undesirable if the area of interest is very small. Furthermore, it is difficult to make a wire electrode which has a very small diameter (i.e., width). The smaller the diameter, the smaller the cross-sectional area and the finer the electrode. Finer electrodes make finer cuts. An instrument with very fine electrodes can be used in tight crevices and in small areas, such as certain predefined regions of the brain. It is also a desirable goal for electrodes to have low resistance so that only a small amount of power need be applied to the electrodes to effectively cut and coagulate the desired tissue. By using less power at the surgical site, the device can be used in delicate surgical procedures, such as neurosurgery, with less risk of damaging neighboring areas.

Despite the variety of electrodes known in the prior art, there is still a need for a finer electrode which can also concentrate energy in the radial direction, is easy and inexpensive to fabricate, and has relatively low resistance. The present invention fills this need by providing an electrode tip with very fine electrodes that have sharp edges in cross-section and are preferably fabricated by photo chemical machining.

SUMMARY OF THE INVENTION

The present invention in one embodiment provides an electrode for a microsurgical instrument. The electrode has a working portion that is generally loop shaped and has sharp edges in cross-section.

Another embodiment of the invention provides an electrode tip comprising a first and a second electrode. The first electrode has a working portion that is generally loop shaped and has sharp edges in cross-section. The second electrode generally surrounds at least a part of the working portion of the first electrode and is generally spaced from and coplanar with the first electrode.

Yet another embodiment of the invention comprises an electrosurgical instrument having a handle and an electrode tip. The handle has a proximal end and a distal end. The electrode tip includes a first electrode and a second electrode. The first and second electrodes each extend from the distal end and have a working portion that is generally loop shaped and generally rectangular in cross-section. The first and second electrodes are adapted to be connected to opposite poles of a bipolar generator. The second electrode generally surrounds at least a part of the working portion of the first electrode and is generally spaced from and coplanar with the first electrode.

Yet another embodiment of the invention comprises a handle and an electrode tip. The handle has a proximal end and a distal end. The electrode tip includes a first and a second electrode, each extending from the distal end, having a working portion that is generally loop shaped and being rectangular in cross-section. The first and second electrodes are adapted to be connected to opposite poles of a bipolar generator. The second electrode is generally hook shaped, generally hooks around the first electrode, and is generally spaced from and coplanar with the first electrode.

Yet other embodiments of the invention provide methods of fabricating electrodes from a metal blank. In one exemplary fabrication method, an electrode tip is fabricated from a metal blank. The method comprises the steps of defining a pattern, the pattern including an electrode tip, and machining the metal blank as defined by the pattern to form at least the electrode tip. The resultant electrode tip has sharp edges in cross-section.

In another exemplary fabrication method, an electrode is fabricated from a metal blank. The method comprises the steps of creating at least one pattern, the pattern including at least an electrode pattern, placing a negative of the pattern against opposite facing surfaces of a metal blank coated with a photoresist material, the negative of the pattern on the opposite facing surfaces being in registration with each other, exposing and developing the metal blank, and removing photoresist from unexposed, undeveloped areas of the metal blank. Next, the metal blank is exposed to a metal dissolving chemical that etches away the unexposed, undeveloped areas of the metal blank. The resultant piece of metal is suitable for use as at least one electrode and has a shape of the at least one created electrode pattern, and has sharp edges in cross-section.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2 is a transverse sectional view of an electrosurgical instrument in accordance with another preferred embodiment of the present invention, prior to removal of its protective electrode tip guard;

FIG. 4 is an enlarged perspective view of electrodes used in an electrode tip for the instrument in FIG. 1;

FIG. 5 is an enlarged top plan view of the electrode tip in FIG. 4 with a tip mounting superimposed thereon in phantom;

FIG. 6 is an enlarged sectional view of the electrode tip in FIG. 4, taken through line 6—6 of FIG. 4;

DETAILED DESCRIPTION OF PREFERRED EMBODIMENT

Figure 1:
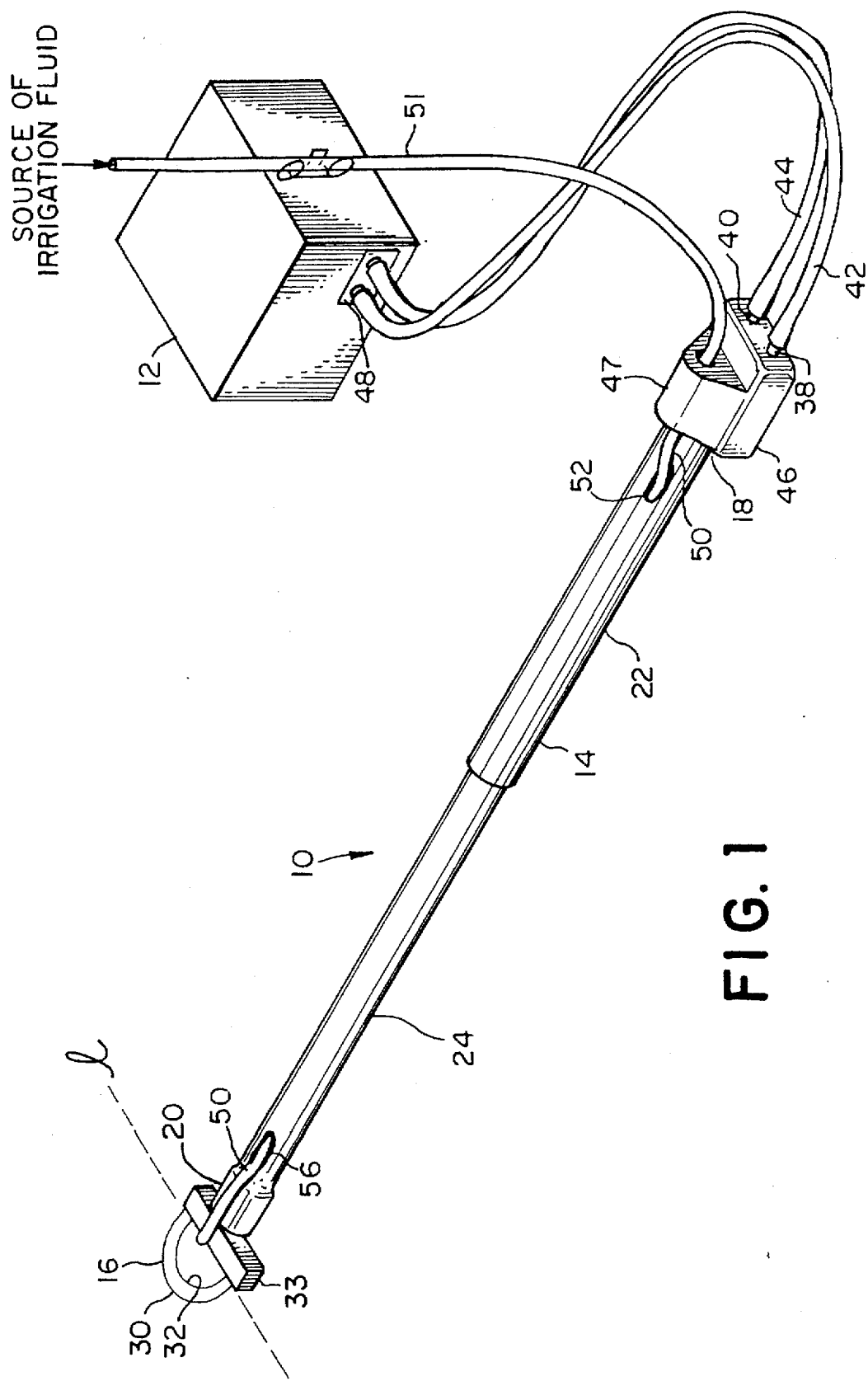
FIG. 1 is a perspective view of an electrosurgical instrument in accordance with a preferred embodiment of the present invention, shown attached to a bipolar generator and ready for use.

Certain terminology is used herein for convenience only and is not be taken as a limitation on the present invention. The words "upper," "lower," "horizontal" and "vertical" designate directions in the drawings to which reference is made. In the drawings, the same reference numerals are employed for designating the same elements throughout the several figures.

Figure 3:
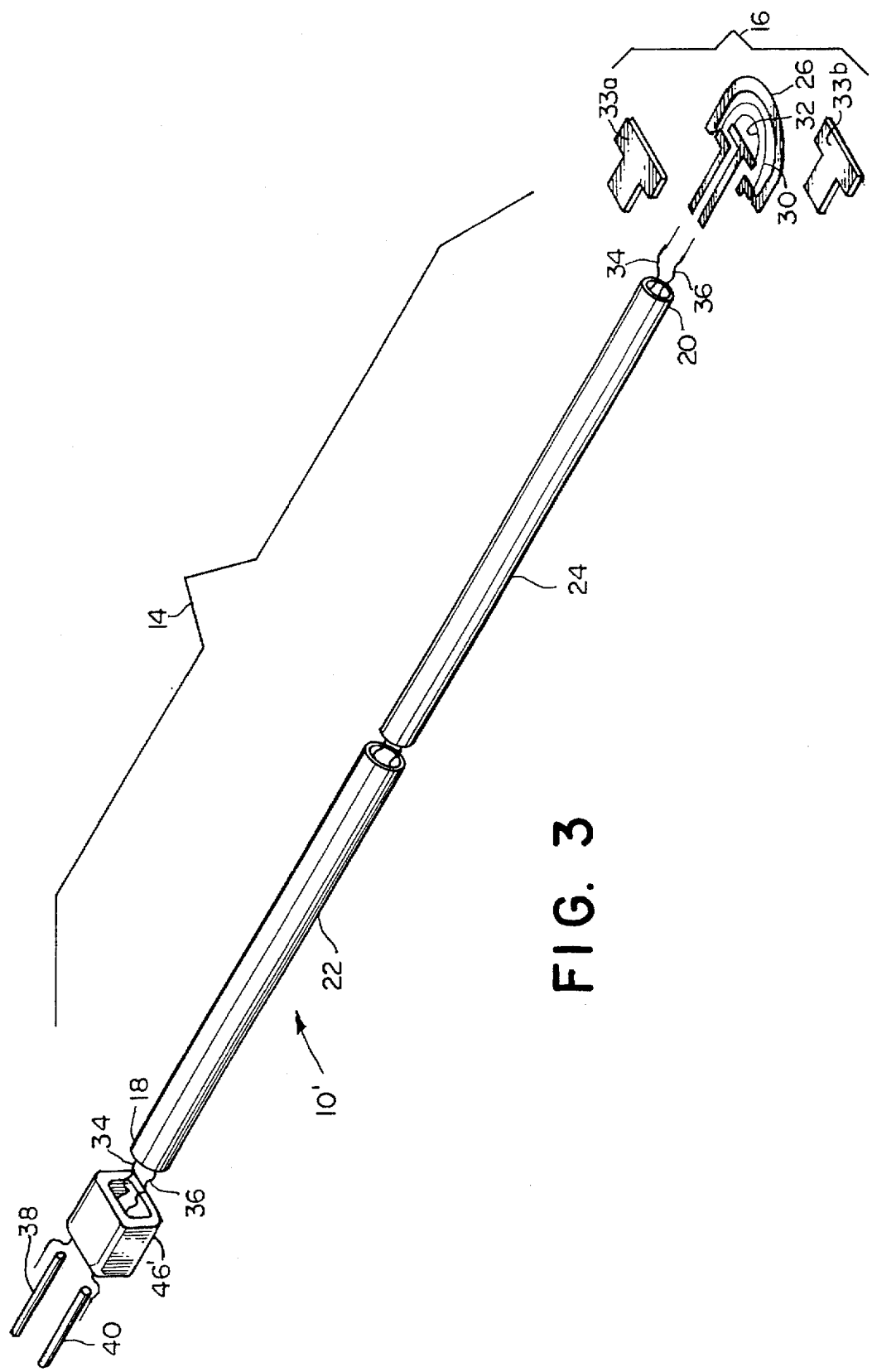
FIG. 3 is an exploded perspective view of the instrument of FIG. 2.

FIG. 1 shows an electrosurgical instrument 10 in accordance with a preferred embodiment of the present invention connected to a radio frequency (RF) output of a bipolar generator 12. Bipolar generators are well-known in the prior art, and thus are not described in detail herein. One bipolar generator suitable for use with the instrument 10 is a CMC III bipolar generator, manufactured by Valley Forge Scientific Corp., Oaks, Pa., described in U.S. Pat. No. 5,318,563 (Malis et al.). FIG. 2 shows internal structure of an instrument 10' and FIG. 3 shows an exploded view of the main components of the instrument 10'. The instrument 10 shown in FIG. 1 differs in two minor ways from the instrument 10' shown in FIGS. 2 and 3. First, the instrument 10' includes a guard 26 integrally formed with the tip of the instrument 10'. The guard 26 is removed before use. In FIG. 1, the guard 26 has already been removed. The guard 26 is described in more detail below. Second, the instrument 10 shown in FIG. 1 includes optional irrigation means, whereas the instrument 10' shown in FIGS. 2 and 3 does not include irrigation means. For clarity, FIGS. 1–3 are described together.

Referring to FIGS. 1–3, the instruments 10 and 10' include a handle 14 and an electrode tip 16. The handle 14 has a proximal end 18 and a distal end 20. The electrode tip 16 extends from the distal end 20. The electrode tip 16 includes a "working portion" which is generally forward of imaginary line 1 and a "non-working portion" or base portion which is generally behind the imaginary line 1 (see FIGS. 1 and 3). The "working portion" comprises that area of the electrode tip 16 which may contact a patient to cut or coagulate. The handle 14 in FIG. 1 is constructed of integrally joined proximal and distal portions 22 and 24 of a high-impact polymeric tubing material, such as extruded styrene. The distal portion 24 partially telescopes into the proximal portion 22 and is secured thereto with adhesive, such as epoxy or cyanoacrylate. Alternatively, the handle 14 may be constructed as a unitary piece. The handle 14 may optionally have circular spaced ribs (not shown) for enhanced gripping. The electrode tip 16 includes a pair of conductive metal electrodes, an outer electrode 30 and an inner electrode 32, both of which include a portion which extends from the distal end 20 of the handle 14. The structure of the electrodes 30 and 32 is described in more detail below. However, FIG. 3 (and also FIG. 4) clearly shows that the outer and inner electrodes 30 and 32 are not physically connected to each other and thus some means are required for maintaining a desired spacing therebetween.

Accordingly, a T-shaped tip mounting 33 (FIG. 1) of nonconductive material maintains the outer and inner electrodes 30 and 32 a fixed distance from each other and physically secures the electrode tip 16 to the distal end of the handle 14. FIG. 3 shows that the tip mounting 33 is formed from two identical T-shaped pieces of nonconductive material 33a and 33b, portions of the electrode tip 16 being sandwiched therebetween. That is, portions of the electrode tip 16 are encased within the tip mounting 33. The imaginary line 1 is colinear with the front edge of the tip mounting 33.

Still referring to FIGS. 1–3, each of the electrodes 30 and 32 are connected to one end of a respective insulated conductor which extends through the handle 14 from the proximal end 18 to near the distal end 20. Thus, the electrode 30 is connected to one end of a first insulated conductor 34 and the electrode 32 is connected to one end of a second insulated conductor 36. The other ends of the first and second conductors 34 and 36 terminate in respective connection pins 38 and 40. The insulation on opposite ends of the conductors 34 and 36 is removed to electrically connect the conductors 34 and 36 to the electrodes 30 and 32 at one end, and to the pins 38 and 40 at the other end. Referring to FIG. 1, conductive wires 42 and 44 are connected at one of their ends to the connection pins 38 and 40, respectively, and are connected at the other of their ends to opposite poles of an isolated output 48 of the bipolar generator 12.

The instruments 10 and 10' each include an end cap 46 and 46', respectively, for sealing the proximal end 18 of the handle tubing and for supporting the connection pins 38 and 40. The end cap 46 of the instrument 10 includes additional structure to support an irrigation tube associated with the irrigation means, as described below.

Referring to FIG. 1, an optional irrigation fluid tube 50 extends through the handle 12 for delivering irrigation fluid to the surgical site. One end of the fluid tube 50 is connected to a luer adapter (not shown) inside of the end cap 46. The other end preferably terminates at the distal edge of the tip mounting 33, preferably extending about 1/16" beyond the tip mounting surface. The fluid tube 50 enters the tubular handle 14 through an inlet port 52 near the proximal end 18, and exits the handle 14 through an outlet port 56 near the distal end 20 (which, when the instrument 10 is in use, is near the surgical site). The end cap 46 includes an extension 47 with a bore for supporting the irrigation tube 50 at the end of the handle 10. The luer is inside of the extension 47. Irrigation tubing 51 is connected at one end to the luer and at the other end to a source of irrigation fluid (not shown). Irrigation fluid (e.g., saline) from the fluid source is thus delivered through the tubing 51, luer, and tube 50 to the surgical site.

To join the electrodes 30 and 32 into a single, unitary electrode tip 16 which can be secured to the handle 14, part of non-working portions of each of the electrodes 30 and 32 are sandwiched between two nonconductive T-shaped pieces of material 33a and 33b, best shown in FIG. 3. In a preferred embodiment of the invention all of the non-working portions are sandwiched between the pieces of material 33a and 33b, except for terminal ends of the electrodes 30 and 32. In a preferred embodiment of the invention, the pieces of material 33a and 33b are plate-like pieces of polymeric material, ultrasonically bonded to each other, to firmly hold the electrodes 30 and 32 in a fixed position with respect to each other. Alternatively, the pieces of material 33a and 33b may be cast ceramic material held together with adhesive. Together, the pieces of material 33a and 33b form a tip mounting 33. To mount the electrode tip 16 to the handle 14, the distal end 20 of the handle 14 is heated to a pliable state. Next, the vertical portion of the tip mounting 33 is inserted into the distal end 20. As the distal end 20 cools, it conforms to and grips the vertical portion of the tip mounting 33. The bond may be further strengthened with adhesive, such as epoxy or cyanoacrylate.

In another embodiment of the invention, the electrode tip 16 is secured to a handle without using the tip mounting 33. In this alternative embodiment, the handle is longitudinally divided into an upper half and lower half. The portions of the electrode tip 16 behind the imaginary line 1 are seated into grooves formed in the lower half of the handle, and terminal ends of the two electrodes make positive electrical connection to respective ends of the conductors 34 and 36. Next, the upper half of the handle is placed over the lower half and secured thereto. The electrode tip 16 is thus held in place by being partially seated into the grooves and sandwiched between the upper and lower halves of the handle. Other means for securing the electrode tip 16 to the handle are within the scope of the invention.

FIGS. 4–6 show additional details and parameters of the electrode tip 16, absent the guard 26 and tip mounting 33. In FIG. 5, the tip mounting 33 is superimposed on the electrode tip 16 in phantom. As described above, the electrode tip 16 has a working portion and a base portion. In addition, each of the electrodes 30 and 32 includes a working portion and a base portion. The working portions of each electrode include the exposed loop parts of the electrodes (i.e., the portions of the electrodes 30 and 32 which are external to the tip mounting 33 and forward of the imaginary line 1). The remaining parts one the electrodes 30 and 32 (the parts enclosed by the tip mounting 33) define the base portion.

Referring to FIGS. 4 and 5, the electrode 30 includes a working portion 80 and a base portion 82, and the electrode 32 includes a working portion 84 and a base portion 86. The base portion 86 comprises a horizontal section 94 and a lead or vertical section 92. The horizontal section 94 bridges opposite ends of the looped working portion 84. The vertical section 92 is connected at one end to the horizontal section 94. The free end of the vertical section 92 is electrically connected to conductor 36, as shown in FIGS. 2 and 3. Together, the working portion 84 and horizontal section 94 define a closed loop.

The base portion 82 of electrode 32 comprises L-shaped sections 90 and 91 extending from opposite ends of the looped working portion 80. The L-shaped section 90 includes a horizontal section 96 and vertical section 97. The L-shaped section 91 also includes a horizontal section 98 and vertical section 99. The horizontal section 96 is connected at one end to an end of the looped working portion 80, and at the other end to the vertical section 97. The free end of the vertical section 97 is used to secure the electrode 30 in proper registration with the electrode 32 via the tip mounting 33 and to inhibit horizontal movement of the electrode 30 within the tip mounting 33. The horizontal section 98 is connected at one end to the other end of the looped working portion 80, and at the other end to the vertical section 99. The free end of the vertical section 99 is electrically connected to conductor 34, as shown in FIGS. 2 and 3. Together, the horizontal sections 96 and 98 and the working portion 80 define an almost closed loop which generally surrounds the closed loop of the electrode 30. Alternatively, the horizontal sections 96 and 98 and the working portion 80 may be viewed as defining a hook shape which hooks almost completely around the closed loop of the electrode 32. Since the two electrodes 30 and 32 are coplanar and cannot come into electrical contact with each other, the electrode 30 cannot, by design, form a closed loop completely around the electrode 32.

FIG. 5 shows a top plan view of the electrode tip 16 in FIG. 4. FIG. 5 also shows regions of the two electrodes 30 and 32 which are encased within the tip mounting 33, shown in phantom. As described above, the electrode 30 generally surrounds the electrode 32 and is generally spaced from and coplanar with the electrode 32. More precisely, either all or at least a part of the working portion 80 of the electrode 30 surrounds either all or at least a part of the working portion 84 of the electrode 32. In FIG. 5, the entire working portion 80 surrounds the entire working portion 84. As also described above, there is a predetermined distance between the electrodes 30 and 32. In one preferred embodiment of the invention, the predetermined distance or spacing, s, is generally equal along the entire path or shape of the electrodes 30 and 32. In another preferred embodiment of the invention, the spacing s is equal between the working portions 80 and with different spacings allowed between the base portions 82 and 94. However, there is always some finite spacing between the electrodes 30 and 32 (i.e., s>0) so that the two electrodes 30 and 32 are never in direct electrical contact with each other. In the example where the spacing s between the working portions 80 and 84 of the electrodes 30 and 32 is equal, it can be said that the electrode 30 is equidistant from the electrode 32. In the figures, the spacing s is equal along the entire path of the electrodes 30 and 32. The scope of the invention also includes embodiments wherein the spacing s between the working portions 80 and 84 of the electrodes 30 and 32 is unequal. For example, the spacing s near the apex of the arc defined by the working portions may be different than the spacing s near the edge regions of the working portions. It may be desirable to have greater or less spacing s near the apex of the arc defined by the working portions than near the edge regions of the working portions.

The electrode tip 16 and electrodes 30 and 32 have defined dimensions and parameters. The tip mounting 33 is shown in FIG. 5 because certain dimensions of the electrode tip 16 are defined in relationship to the tip mounting 33, or to other structure that performs the same function as the tip mounting 33. The maximum horizontal distance of the electrode tip 16 is defined as the width, $w_t$, of the working portion 84 of the electrode 32. The width, $w_t$, is the distance between opposite exposed ends of the working portion 84 of the electrode 32. The height of the electrode tip 16 is defined as the height, $h_t$, from the opposite exposed ends of the working portion 84 of the electrode 32 to apex 100 of the arc in the working portion 84 of the electrode 32. (The height of the electrode tip 16 is thus defined by dimensions of the inner electrode 32, not the outer electrode 30.) The electrode tip 16 also has a loop ratio, defined as the ratio of the absolute distance of the working portion 84 vs. the absolute distance of the working portion 80. The leads or vertical sections 98 and 92 have predefined lengths $l_{e1}$ and $l_{e2}$, respectively.

Referring to FIGS. 4, 5 and 6 (especially, FIG. 6), the working portion 80 of the electrode 30 has a flat upper surface 102, a flat lower surface 104, and squared off sharp corners or edges 106. Likewise, the working portion 84 of the electrode 32 has a flat upper surface 108, a flat lower surface 110, and squared off sharp corners or edges 112. In the embodiment of the invention shown in the figures, the base portions 82 and 86 also have flat upper and lower surfaces, and sharp edges, due to the method of fabricating the electrodes 30 and 32. The base portions 82 and 86 need not have either of these features. The working portions 80 and 84 are circumferentially unattached to any surrounding structure, and the material of the electrodes 30 and 32 is continuous (i.e., unbroken) through their respective working portions 84 and 80. As a result of these features, at least the working portions 80 and 84 of the electrodes 30 and 32 are generally rectangular in cross-section and thus are defined by a thickness and a width. The area of the rectangular cross-section is generally uniform throughout the working portion. Since the electrodes 30 and 32 are coplanar, they have equal thicknesses, $t_e$. The widths of the electrode working portions 80 and 84 may be equal or different. In the figures, the electrodes 30 and 32 have different working portion widths $w_{e1}$ and $w_{e2}$, respectively. Widths of the horizontal sections 94, 96 and 98, and the leads or vertical sections 92 and 99 are significantly larger than the widths of the working portion 80 and 84. A preferred embodiment of the electrode tip 16, has the following approximate range of dimensions and parameters:

| | |
|---|---|
| spacing, (s) | 0.035" (0.89 mm.) |
| width of electrode tip ($w_t$) | 0.20" to 0.98" (5 mm. to 25 mm.) |
| height of electrode tip ($h_t$) | 0.20" to 0.59" (5 mm. to 15 mm.) |
| length of vertical section 99 ($l_{e1}$) | 0.50" (12.7 mm.) |
| length of vertical section 92 ($l_{e2}$) | 0.54" (13.6 mm.) |
| loop ratio | 1:1½ |
| thickness of electrodes ($t_e$) | 0.005" to 0.015" (0.13 mm. to 0.38 mm.) |
| width of electrode 30 ($w_{e1}$) | 0.009" (0.23 mm.) |
| width of electrode 32 ($w_{e2}$) | 0.006" (0.15 mm.) |
| width of horizontal sections 90, 94 and 96 | 0.059" (1.5 mm.) |
| width of vertical sections 92 and 98 | 0.039" (1.0 mm.) |
| electrode 30 and 32 material | stainless steel, tungsten, titanium, tungsten deposited on stainless steel, INCONEL, (a nickel and chromium alloy) or other metallic alloys |

Some examples of suitable width and height combinations for electrode tips include 25×15, 20×10, 20×7, 15×10, 15×7, 10×10, 10×7, 5×10, 5×5 and 3×5, wherein the first dimension is the width ($w_t$) in mm. and the second dimension is the height ($h_t$) in mm. FIGS. 4–6 show a 20×10 mm. tip having a thickness of about 0.015" (0.38 mm.).

Figure 7:
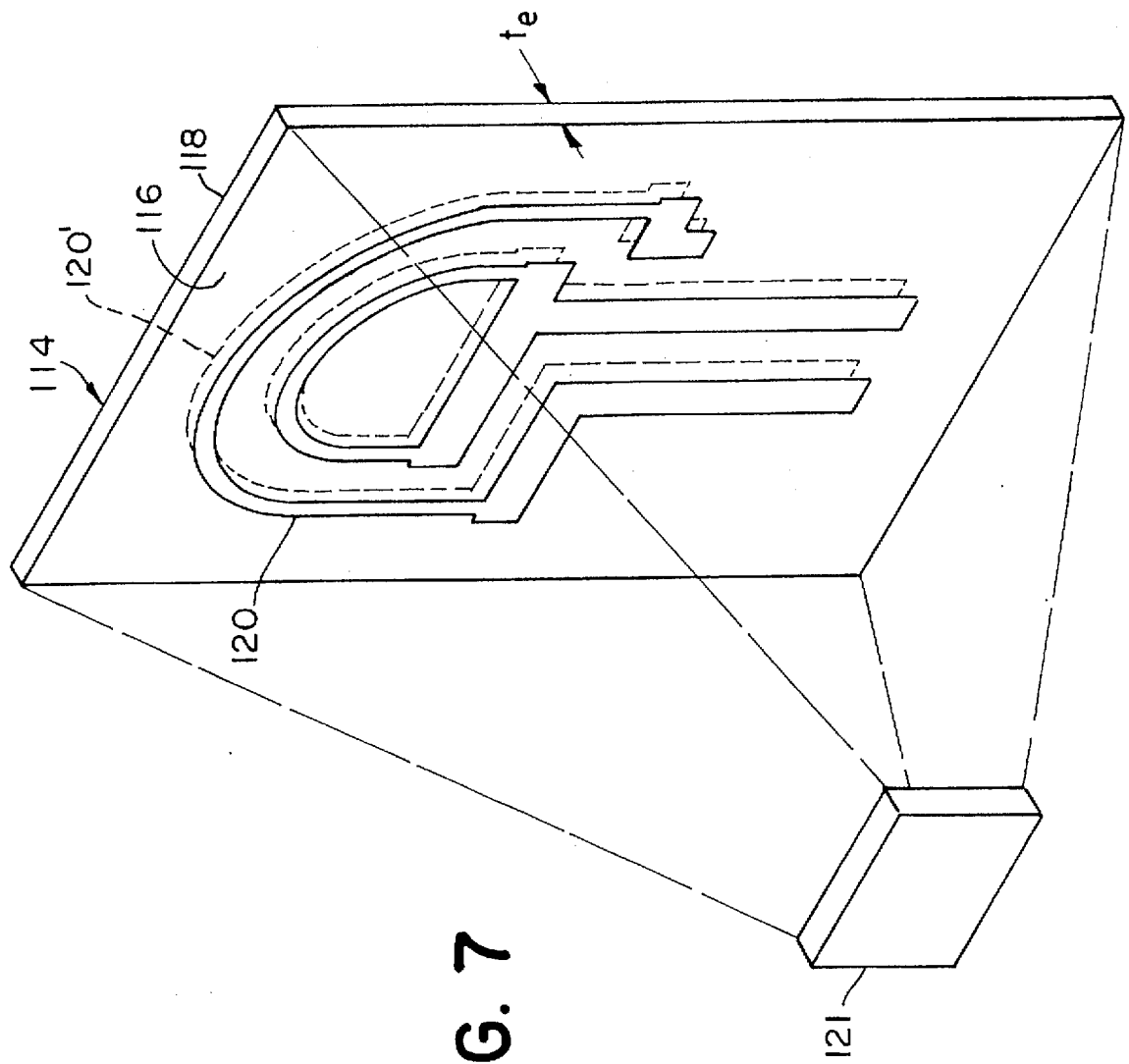
FIG. 7 is a blank of metal showing an electrode tip pattern for making an electrode tip for the instrument in FIG. 2.
Figure 8:
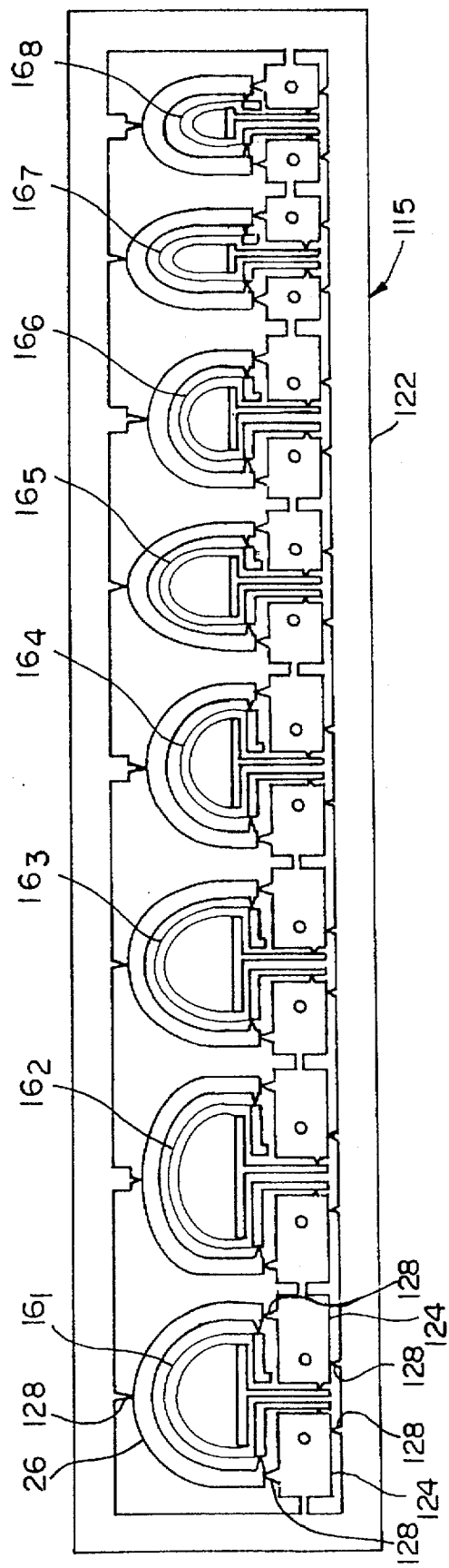
FIG. 8 shows a plurality of electrode tips for the instrument of FIG. 2, simultaneously formed from a single metal blank, and prior to being detached therefrom.

One preferred method of fabricating the electrode tip 16 is by photo chemical machining. Referring to FIG. 7, the process begins with a metal blank 114, such as stainless steel, having a thickness $t_e$ and flat upper and lower surfaces 116 and 118. The metal blank 114 is precoated with photoresist materials of common usage. A pattern 120 and its mirror image 120' are created by standard drafting techniques and are photographically transferred (in negative form) to transparent film. The patterns 120 and 120' may also be reduced in size to reduce drawing line widths and to achieve proper final product size. Next, properly sized patterns 120 and 120' are placed in contact with respective upper and lower surfaces 116 and 118 of the metal blank 114, in proper registration and alignment with each other. The pattern 120 on the upper surface 116 is in solid lines and the pattern 120' on the lower surface 118 is in phantom. Using a vacuum table (not shown), the upper and lower patterns 120 and 120' are held closely to the metal blank 114 while an arc lamp 121 exposes the photoresist in the area where the negative patterns are transparent. Next, the metal blank 114 is removed and developed in the same manner as a negative photograph is developed. The developing process chemically hardens the photoresist in areas exposed to the arc lamp 121. The unexposed and undeveloped photoresist is washed away. Next, the metal blank 114 is exposed to chemicals commonly used in the art to dissolve metal not covered with photoresist. Chromic acid, ferric chloride, or other etch chemicals may be used. After etching, the remaining metal is a faithful reproduction, in metal, of the pattern 120, including at least the electrodes, a carrier and a protective guard structure, and support and tab structures, all for use during post-manufacturing handling. For simplicity, FIG. 7 does not show the patterns which form the additional non-electrode structures. These patterns are shown in FIG. 8.

The resultant piece of metal has the shape of the created pattern, and is thus identical to FIGS. 4 and 5. That is, the resultant piece of metal is the shape of the electrodes 30 and 32. Since the metal blank 114 has flat upper and lower surfaces 116 and 118, the resultant electrodes 30 and 32 are coplanar and have sharp edges in cross-section. The resultant electrode tip 16 (i.e., electrodes 30 and 32) is mounted or inserted into the distal end 20 of the handle 14 and engages conductors 34 and 36 to establish positive electrical contact therebetween, as shown in FIG. 3, to create the electrosurgical instrument 10.

The electrode tip 16 is very delicate and should be protected from physical contact until it is ready to be used. Also, the relative registration of the electrodes 30 and 32 must be maintained because the two electrodes are not physically connected to each other at any point. To protect the electrode tip 16 and to maintain proper relative registration between the electrodes 30 and 32, it is preferred to fabricate the electrode tip 16 with a guard, supports, a carrier and tabs therebetween, and to install the tip mounting 33 after fabrication but before removal of the supports 124 or guard 26.

When electrode tips 16 are made by the process described above, plural electrode tips 16 of the same or different width and height combinations may be simultaneously fabricated from a single metal blank. Thus, significant manufacturing efficiencies can be achieved.

FIG. 8 shows eight electrode tips $16_1$ through $16_8$ fabricated from a single metal blank 115 and illustrates all of these above-mentioned features. In FIG. 8, each electrode tip $16_1$ through $16_8$ has a different width and height combination. Prior to being etched, a pattern including (1) a peripheral carrier pattern, (2) an electrode pattern for each of the electrode tips $16_1$ through $16_8$, and (3) associated support patterns, tab patterns and a guard pattern for each electrode pattern, is placed against both surfaces of the metal blank 115, as described above. The patterns form the electrode tips $16_1$ through $16_8$, peripheral carrier 122, support plates or supports 124, guards 26 and tabs 128 in the resultant metal blank of FIG. 8. To install a particular electrode tip 16 into a handle 14, an electrode tip 16 and corresponding supports 124 and guard 26 is removed from the carrier 122. Next, non-working portions of the electrode tip 16 are sandwiched between the two T-shaped pieces of material 33a and 33b. The pieces of material 33a and 33b are secured to each other and to the electrode tip 16, such as by ultrasonic bonding to form the tip mounting 33. (Alternatively, the non-working portions of the electrode tip 16 may be sandwiched between the two T-shaped pieces of material 33a and 33b while the electrode tip 16 is still in the carrier 122.) The tip mounting 33 encases all but the working portion of the electrode tip 16 and the terminal ends of each individual electrode. As a result, the tip mounting 33 maintains relative registration of the working portions of the two electrodes. Next, the supports 124 and related tabs 128 are removed. One end of the first and second conductors 34 and 36 are connected to respective terminal ends of the electrodes 30 and 32, such as by soldering or welding. The conductors 34 and 36 are fitted through the distal portion of the handle 14. The electrode tip 16, with the guard 26 still intact, is then installed into the distal end of the distal portion 24 of the handle 14, in accordance with the procedure described above with respect to FIGS. 1–3. FIG. 2 shows one such guard 26 attached to the electrode tip 16 of a fully assembled instrument 10. Immediately before use, the guard 26 is snapped off.

While the photo chemical etching process is used to fabricate the entire electrode tip 16 in one step, the method may be used to separately fabricate each electrode 30 and 32. The photo chemical etching process may be replaced by other processes which can achieve a similar result from a metal blank. Other potential techniques include laser cutting, mechanical microcutting techniques or other techniques which can form electrodes having sharp edges and working portion dimensions defined above.

When fabricating electrode tips by the process shown in FIG. 8, the tips may be colored to quickly identify different sized electrodes. For example, titanium electrodes tips may be colored by anodizing.

Electrode tip sizes are selected according to the desired application (e.g., neurosurgery, obstetrics/gynecology surgery) and structure of the surgical site. For example, a long, narrow tip should be used when the surgical site is a narrow cavity.

The guard 26 may be replaced by other guard structure which need not be integrally formed with the electrode tip 16. It is also within the scope of the invention to make the electrodes 30 and 32 without the carrier 122, supports 124, guards 26 and tabs 128. Instead, the electrodes 30 and 32 may be carefully handled after fabrication and secured in a fixed relationship to each other, and to a handle, by other suitable means.

The instrument 10 is meant to be disposable, although it is within the scope of the invention to reuse any parts of the instrument 10 which are not degraded during use and which can be adequately sterilized.

The loop shaped working portion of the electrodes 30 and 32 may be generally circular, semicircular, parabolic or rectangular in shape.

The electrodes 30 and 32 in the present instrument have sharp edges 106 and 112 in cross-section, in contrast to prior art wire electrodes which do not have sharp edges in cross-section. The sharp edges concentrate the contact area and improve the concentration of energy at the surgical site in comparison to the wire electrodes. In use, when power is applied to the electrode tip 16, energy distributes evenly along the length of the electrode working portions 80 and 82. The energy also emits radially from the working portions 80 and 82. However, the emitted RF energy concentrates and focuses at the edges 106 and 112 instead of radially emitting equally in all directions as in prior art wire electrodes. For at least this reason, the electrodes 30 and 32 formed by the process described above evidence lower resistance to cutting than the prior art wire electrodes. Thus, less power may be applied to the electrodes 30 and 32 to achieve the same cutting/coagulating effect as the prior art wire electrodes. By using less power at the surgical site, the device can be used in delicate surgical procedures, such as neurosurgery, with less risk of disturbing neighboring tissue or organs.

Furthermore, the electrodes 30 and 32 may be fabricated to be significantly finer than what is currently achievable using wire electrodes. For example, the smallest disclosed wire diameter in U.S. Pat. Nos. 5,282,799 (Rydell) and 5,192,280 (Parins) is 0.010 inches (0.254 mm.), providing a cross-sectional area of 0.05 $mm^2$ ($0.7854 \times d^2 = 0.7854 \times (0.254)^2 = 0.05$). In contrast, electrode 30 may have a width as small as about 0.006" (0.15 mm.) and a thickness as small as 0.005" (0.13 mm.), thereby providing a cross-sectional area as small as about 0.02 $mm^2$ ($w \times t = 0.15 \times 0.13 = 0.02$), measurably finer than the cross-sectional area of the wire electrode.

Referring to FIG. 6, the electrodes 30 and 32 are ideally rectangular in cross-section. However, it is difficult to produce perfectly rectangular shaped electrodes using the chemical etching process described herein. The fabricated electrodes may have regions of slight concavity along the side edges, giving a slightly hourglass shape to the electrodes in cross-section. Such electrodes still possess the advantages described above because they still have relatively sharp edges. One way to minimize the concavity when etching from one side only is to etch about halfway through the blank, and then turn the blank over and etch through the other side.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An electrode tip for an electrosurgical instrument, the electrode tip comprising an electrode, the electrode having a working portion that is generally loop shaped and has sharp edges in cross-section, the working portion being generally rectangular in cross-section and circumferentially unattached to any surrounding structure, wherein the working portion has a cross-sectional width of about 0.15 mm or about 0.23 mm.

2. An electrode tip according to claim 1 wherein the generally loop shaped working portion of the electrode is generally circular, semicircular, parabolic or rectangular in shape.

3. An electrode tip according to claim 1 wherein the electrode is formed from the group of materials consisting of stainless steel, tungsten, a nickel and chromium alloy and titanium.

4. An electrode tip according to claim 1 wherein the electrode has cross-sectional thickness of about 0.13 mm to about 0.38 mm.

5. An electrode tip according to claim 1 wherein the area of the rectangular cross-section is generally uniform throughout the working portion.

6. An electrode tip according to claim 1 wherein the electrode material is continuous through the working portion.

7. An electrode tip for an electrosurgical instrument comprising:
   (a) a first electrode having a working portion that is generally loop shaped and has sharp edges in cross-section; and
   (b) a second electrode having a working portion that is generally loop shaped and has sharp edges in cross-section, the second electrode generally surrounding at least a part of the working portion of the first electrode, the second electrode being generally spaced from and coplanar with the first electrode.

8. An electrode tip according to claim 7 wherein the first and second electrodes are generally rectangular in cross-section.

9. An electrosurgical instrument according to claim 7 wherein the spacing between the working portions of the first and second electrodes is generally equal along the entire length of the working portions.

10. An electrode tip according to claim 7 wherein the first electrode is a closed loop.

11. An electrode tip according to claim 7 wherein the second electrode is an almost closed loop.

12. An electrode tip according to claim 7 wherein the first electrode is a closed loop and the second electrode is an almost closed loop.

13. An electrode tip according to claim 7 wherein the generally loop shaped working portion of the first and second electrodes are generally circular, semicircular, parabolic or rectangular in shape.

14. An electrode tip according to claim 7 wherein the first and second electrodes are formed from the group of materials consisting of stainless steel, tungsten, a nickel and chromium alloy, and titanium.

15. An electrosurgical instrument comprising:
 (a) a handle having a proximal end and a distal end; and
 (b) an electrode tip, the tip including
  (i) a first electrode extending from the distal end, the first electrode having a working portion that is generally loop shaped and is generally rectangular in cross-section, the first electrode adapted to be connected to one pole of a bipolar generator, and
  (ii) a second electrode extending from the distal end, the second electrode having a working portion that is generally loop shaped and is generally rectangular in cross-section, the second electrode adapted to be connected to the other pole of the bipolar generator, the second electrode generally surrounding at least a part of the working portion of the first electrode, the second electrode being generally spaced from and coplanar with the first electrode.

16. An electrosurgical instrument according to claim 15 further comprising:
 (c) first and second conductors each connected at one end to the respective first and second electrodes and adapted for being connected at the other end to the respective poles of the bipolar generator, the first and second conductors extending through the handle from the proximal end to the distal end.

17. An electrosurgical instrument according to claim 15 wherein the spacing between the working portions of the first and second electrodes is generally equal along the entire length of the working portions.

18. An electrosurgical instrument according to claim 15 wherein the first electrode is a closed loop.

19. An electrosurgical instrument according to claim 15 wherein the second electrode is an almost closed loop.

20. An electrosurgical instrument according to claim 15 wherein the first electrode is a closed loop and the second electrode is an almost closed loop.

21. An electrosurgical instrument according to claim 15 wherein the generally loop shaped working portion of the first and second electrodes are generally circular, semicircular, parabolic or rectangular in shape.

22. An electrosurgical instrument according to claim 15 wherein the first and second electrodes are formed from the group of materials consisting of stainless steel, tungsten, a nickel and chromium alloy, and titanium.

23. An electrosurgical instrument according to claim 15 further comprising:
 (c) an irrigation conduit extending through the handle from the proximal end to the distal end for delivering irrigation fluid to the distal end.

24. An electrosurgical instrument according to claim 15 wherein the first and second electrodes include non-working portions, the instrument further comprising:

(c) a tip mounting for maintaining the first and second electrodes in the spaced relationship and for attaching the electrode tip to the handle, the tip mounting formed from first and second generally T-shaped pieces of material attached to each other, at least a part of the non-working portions of the first and second electrodes being sandwiched between the first and second T-shaped pieces of material, a vertical portion of the tip mounting being attached to the handle.

25. An electrosurgical instrument comprising:
 (a) a handle having a proximal end and a distal end; and
 (b) an electrode tip, the tip including
  (i) a first electrode extending from the distal end, the first electrode having a working portion that is generally loop shaped and is generally rectangular in cross-section, the first electrode adapted to be connected to one pole of a bipolar generator, and
  (ii) a second electrode extending from the distal end, the second electrode being generally hook shaped and having a working portion that is generally rectangular in cross-section, the second electrode adapted to be connected to the other pole of the bipolar generator, the second electrode generally hooking around the first electrode, the second electrode being generally spaced from and coplanar with the first electrode.

26. An electrosurgical instrument according to claim 25 wherein the second electrode hooks almost completely around the first electrode.

27. An electrode tip for an electrosurgical instrument, the electrode tip comprising an electrode, the electrode having a working portion that is generally loop shaped and has sharp edges in cross-section, the electrode having only one end adapted to be connected to a conductor, and the working portion being circumferentially unattached to any surrounding structure.

28. An electrode tip according to claim 27 wherein the electrode is generally rectangular in cross-section.

29. An electrode tip according to claim 27 wherein the electrode material is continuous through the working portion.

30. An electrosurgical instrument comprising:
 (a) a handle having a proximal end and a distal end; and
 (b) an electrode tip including an electrode extending from the distal end, the electrode having a working portion that is generally loop shaped and has sharp edges in cross-section, the electrode including a single lead section for attachment of the electrode to one pole of a bipolar generator, and the working portion being circumferentially unattached to any surrounding structure.

31. An electrosurgical instrument according to claim 30 wherein the electrode is generally rectangular in cross-section.

32. An electrosurgical instrument according to claim 30 wherein the electrode material is continuous through the working portion.

33. An electrosurgical instrument comprising:
 (a) a handle having a proximal end and a distal end; and
 (b) an electrode tip directly connected to, and supported by, the handle, the electrode tip including an electrode having a working portion that is generally loop shaped and has sharp edges in cross-section, the working portion being circumferentially unattached to any surrounding structure, wherein the working portion has a cross-sectional width of about 0.15 mm or about 0.23 mm.

34. An electrosurgical instrument according to claim 33 wherein the electrode is generally rectangular in cross-section.

35. An electrosurgical instrument according to claim 33 wherein the electrode material is continuous through the working portion.

36. An electrode tip for an electrosurgical instrument, the electrode tip comprising an electrode, the electrode having a working portion that is generally loop shaped and has sharp edges in cross-section, the working portion being generally rectangular in cross-section and circumferentially unattached to any surrounding structure, wherein the working portion has a cross-sectional thickness of about 0.13 mm to about 0.38 mm.

37. An electrode tip according to claim 36 wherein the working portion has a cross-sectional width of about 0.15 mm or about 0.23 mm.

38. An electrode tip according to claim 36 wherein the generally loop shaped working portion of the electrode is generally circular, semicircular, parabolic or rectangular in shape.

39. An electrode tip according to claim 36 wherein the electrode is formed from the group of materials consisting of stainless steel, tungsten, a nickel and chromium alloy and titanium.

40. An electrode tip according to claim 36 wherein the area of the rectangular cross-section is generally uniform throughout the working portion.

41. An electrode tip according to claim 36 wherein the electrode material is continuous through the working portion.

42. An electrosurgical instrument comprising:

(a) a handle having a proximal end and a distal end; and (b) an electrode tip directly connected to, and supported by, the handle, the electrode tip including an electrode having a working portion that is generally loop shaped and has sharp edges in cross-section, the working portion being circumferentially unattached to any surrounding structure, wherein the electrode has a cross-sectional thickness of about 0.13 mm to about 0.38 mm.

43. An electrosurgical instrument according to claim 42 wherein the electrode is generally rectangular in cross-section.

44. An electrosurgical instrument according to claim 42 wherein the electrode material is continuous through the working portion.

* * * * *